(12) United States Patent
West

(10) Patent No.: US 7,648,710 B2
(45) Date of Patent: *Jan. 19, 2010

(54) FORMULATION CONTAINING PHOSPHATE DERIVATIVES OF ELECTRON TRANSFER AGENTS

(75) Inventor: Simon Michael West, Williamstown (AU)

(73) Assignee: Vital Health Sciences Pty Ltd., Melbourne (AU)

( * ) Notice: Subject to any disclaimer, the term of this patent is extended or adjusted under 35 U.S.C. 154(b) by 45 days.

This patent is subject to a terminal disclaimer.

(21) Appl. No.: 10/416,775

(22) PCT Filed: Nov. 14, 2001

(86) PCT No.: PCT/AU01/01475

§ 371 (c)(1),
(2), (4) Date: Dec. 23, 2003

(87) PCT Pub. No.: WO02/40033

PCT Pub. Date: May 23, 2002

(65) Prior Publication Data

US 2004/0096493 A1    May 20, 2004

(30) Foreign Application Priority Data

Jun. 6, 2001    (AU) ................... PR5499

(51) Int. Cl.
*A61K 8/02* (2006.01)
(52) U.S. Cl. ................... 424/401; 549/220
(58) Field of Classification Search ................... 424/401; 514/100
See application file for complete search history.

(56) References Cited

U.S. PATENT DOCUMENTS

| | | | |
|---|---|---|---|
| 2,407,823 A | 9/1946 | Fieser | |
| 2,667,479 A | 1/1954 | Hoffman et al. | |
| 2,913,477 A | 11/1959 | Hirschmann | |
| 3,127,434 A | 3/1964 | Andrews | |
| 3,212,901 A | 10/1965 | Robeson | |
| 4,075,333 A | 2/1978 | Josse | |
| 4,141,938 A | 2/1979 | Klose | |
| 4,299,906 A | 11/1981 | Liu | |
| 4,369,172 A | 1/1983 | Schor et al. | |
| 4,444,755 A | 4/1984 | Horrobin | |
| 4,654,373 A | 3/1987 | Bertelli | |
| 4,684,520 A | 8/1987 | Bertelli | |
| 4,686,211 A | 8/1987 | Hara et al. | |
| 4,874,883 A | 10/1989 | Uphues et al. | |
| 4,952,495 A | 8/1990 | Belly et al. | |
| 5,041,434 A | 8/1991 | Lubkin | |
| 5,053,222 A | 10/1991 | Takasu et al. | |
| 5,091,848 A | 2/1992 | Kojima | |
| 5,094,848 A | 3/1992 | Brixner | |
| 5,114,957 A | 5/1992 | Hendler et al. | |
| 5,138,084 A | 8/1992 | Casagrande et al. | |
| 5,173,304 A | 12/1992 | Lohner et al. | |
| 5,374,645 A | 12/1994 | Kurihara-Bergstrom et al. | |
| 5,387,579 A | 2/1995 | Meybeck et al. | ............ 514/100 |
| 5,446,070 A | 8/1995 | Mantelle | |
| 5,474,891 A | 12/1995 | Murphy | |
| 5,474,991 A | 12/1995 | Ogata et al. | |
| 5,554,781 A | 9/1996 | Reierson | |
| 5,570,504 A | 11/1996 | Distefano et al. | |
| 5,583,105 A | 12/1996 | Kovacs et al. | |
| 5,589,504 A | 12/1996 | Dannenberg et al. | |
| 5,603,949 A | 2/1997 | Meybeck et al. | |
| 5,607,921 A | 3/1997 | Bernard et al. | |
| 5,643,597 A | 7/1997 | Meybeck et al. | |
| 5,741,518 A | 4/1998 | Ribier et al. | |
| 5,759,526 A | 6/1998 | Simonnet et al. | |
| 5,776,915 A | 7/1998 | Peterson et al. | |
| 5,780,504 A | 7/1998 | Ptchelintsev | |
| 5,804,168 A | 9/1998 | Murad | |
| 5,804,216 A | 9/1998 | Terren et al. | |
| 5,807,542 A | 9/1998 | Challis et al. | |
| 5,807,845 A | 9/1998 | Ogata et al. | |
| 5,885,595 A * | 3/1999 | Corey et al. | ................... 424/401 |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A | 7/1999 | Lucas et al. | |
| 5,952,361 A | 9/1999 | Dias Nahoum | |

(Continued)

FOREIGN PATENT DOCUMENTS

AU    A-64816/94    12/1994

(Continued)

OTHER PUBLICATIONS

Bikerman, J.J., J. Phys. Chem,, vol. 56, 1952, pp. 164-165, XP001203471.

(Continued)

*Primary Examiner*—MP Woodward
*Assistant Examiner*—Bethany Barham
(74) *Attorney, Agent, or Firm*—Michael Best & Friedrich LLP

(57) ABSTRACT

There is provided an emulsion composition for therapeutic administration comprising: (a) at least one mono-electron transfer agent phosphate derivative; (b) at leas tone di-electron transfer agent phosphate derivative; wherein the amount of mono-electron transfer agent phosphate derivatives is no less than equimolar to the amount of di-electron transfer agent phosphate; and (c) a suitable carrier.

14 Claims, No Drawings

U.S. PATENT DOCUMENTS

| | | | | |
|---|---|---|---|---|
| 5,965,750 | A * | 10/1999 | Oonishi et al. | 549/218 |
| 5,981,474 | A | 11/1999 | Manning et al. | |
| 6,022,867 | A | 2/2000 | Ito et al. | |
| 6,046,181 | A | 4/2000 | Oonishi et al. | 514/100 |
| 6,048,891 | A | 4/2000 | Wechter | |
| 6,096,326 | A | 8/2000 | Wikholm | |
| 6,121,249 | A | 9/2000 | Weissman et al. | |
| 6,143,770 | A | 11/2000 | Lane et al. | |
| 6,184,247 | B1 | 2/2001 | Schneider | |
| 6,248,758 | B1 | 6/2001 | Klokkers et al. | |
| 6,384,043 | B1 | 5/2002 | Peyman et al. | |
| 6,403,811 | B1 * | 6/2002 | West | 549/220 |
| 6,417,223 | B1 | 7/2002 | Sanders et al. | |
| 6,423,742 | B1 | 7/2002 | Larson | |
| 6,444,220 | B2 | 9/2002 | Wiley | |
| 6,444,234 | B1 | 9/2002 | Kirby et al. | |
| 6,479,540 | B1 | 11/2002 | Constantinides et al. | |
| 6,503,545 | B1 | 1/2003 | Perlman et al. | |
| 6,579,995 | B1 | 6/2003 | West | |
| 6,599,933 | B2 | 7/2003 | Takata et al. | |
| 6,641,847 | B1 | 11/2003 | Nawar | |
| 6,645,998 | B2 | 11/2003 | Sanders et al. | |
| 6,703,384 | B2 | 3/2004 | Sanders et al. | |
| 6,770,672 | B1 | 8/2004 | Sanders et al. | |
| 7,179,486 | B1 | 2/2007 | Mulye | |
| 2001/0006659 | A1 | 7/2001 | Koike et al. | |
| 2001/0044462 | A1 | 11/2001 | Hensley et al. | |
| 2002/0131994 | A1 | 9/2002 | Schur et al. | |
| 2002/0151467 | A1 | 10/2002 | Leung | |
| 2003/0035812 | A1 | 2/2003 | Ito et al. | |
| 2003/0157326 | A1 | 8/2003 | Vaghefi et al. | |
| 2003/0206972 | A1 | 11/2003 | Babish et al. | |
| 2004/0052754 | A1 | 3/2004 | West et al. | |
| 2004/0067890 | A1 | 4/2004 | Gupta | |
| 2004/0097431 | A1 | 5/2004 | Sanders et al. | |
| 2004/0097472 | A1 | 5/2004 | West et al. | |
| 2004/0204343 | A1 | 10/2004 | Fishman | |
| 2004/0234602 | A1 | 11/2004 | Fischer et al. | |
| 2004/0235938 | A1 | 11/2004 | Sanders et al. | |
| 2004/0241225 | A1 | 12/2004 | West | |
| 2004/0253318 | A1 | 12/2004 | West et al. | |
| 2005/0009787 | A1 | 1/2005 | West et al. | |
| 2005/0089495 | A1 | 4/2005 | West | |
| 2006/0241085 | A1 | 10/2006 | West et al. | |
| 2006/0257459 | A1 | 11/2006 | West et al. | |
| 2006/0281715 | A1 | 12/2006 | West | |
| 2006/0281716 | A1 | 12/2006 | West et al. | |
| 2007/0042999 | A1 | 2/2007 | West et al. | |
| 2007/0135390 | A1 | 6/2007 | West et al. | |
| 2009/0004166 | A1 | 1/2009 | West et al. | |
| 2009/0005348 | A1 | 1/2009 | Ogru et al. | |
| 2009/0036354 | A1 | 2/2009 | Gavin et al. | |
| 2009/0186856 | A1 | 7/2009 | West et al. | |

FOREIGN PATENT DOCUMENTS

| | | |
|---|---|---|
| AU | B-16178/95 | 7/1995 |
| AU | A-32914/95 | 2/1996 |
| AU | A-89312/98 | 1/1998 |
| AU | A-41018/97 | 4/1998 |
| CA | 1337992 | 1/1996 |
| CA | 2426852 | 5/2002 |
| CA | 2426885 | 5/2002 |
| CN | 1173869 | 2/1998 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0617963 | 10/1994 |
| EP | 0641790 | 3/1995 |
| EP | 0661053 | 7/1995 |
| EP | 0669132 | 8/1995 |
| EP | 0674904 | 10/1995 |
| EP | 0679399 | 11/1995 |
| EP | 0680760 | 11/1995 |
| EP | 0684043 | 12/1995 |
| EP | 0699440 | 3/1996 |
| EP | 0826365 | 3/1998 |
| EP | 0845216 | 6/1998 |
| EP | 0699437 | 12/1998 |
| EP | 0965328 | 12/1999 |
| EP | 1023897 | 8/2000 |
| EP | 1053749 | 11/2000 |
| EP | 1264595 | 12/2002 |
| GB | 778142 | 7/1957 |
| GB | 1121683 | 7/1968 |
| GB | 2227662 | 8/1990 |
| JP | 53015381 | 2/1978 |
| JP | 58180410 | 10/1983 |
| JP | 59044375 | 3/1984 |
| JP | 59157091 | 9/1984 |
| JP | 61086940 | 5/1986 |
| JP | 61091137 | 5/1986 |
| JP | 61233631 | 10/1986 |
| JP | 62195393 | 8/1987 |
| JP | 4208209 | 7/1992 |
| JP | 5132700 | 5/1993 |
| JP | 5201858 | 8/1993 |
| JP | 6048962 | 2/1994 |
| JP | 6078214 | 10/1994 |
| JP | 7011291 | 1/1995 |
| JP | 7207298 | 8/1995 |
| JP | 7278587 | 10/1995 |
| JP | 7316170 | 12/1995 |
| JP | 8073338 | 3/1996 |
| JP | 8193089 | 7/1996 |
| JP | 8311085 | 11/1996 |
| JP | 8311489 | 11/1996 |
| JP | 8325594 | 12/1996 |
| JP | 9044375 | 2/1997 |
| JP | 10045783 | 2/1998 |
| JP | 10155429 | 6/1998 |
| JP | 11043436 | 2/1999 |
| JP | 11-199424 | 7/1999 |
| JP | 11-199465 | 7/1999 |
| JP | 2001247585 | 9/2001 |
| JP | 2002080475 | 3/2002 |
| SU | 925961 | 5/1982 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 93/02661 | 2/1993 |
| WO | WO 93/15731 | 8/1993 |
| WO | WO 93/24131 | 12/1993 |
| WO | WO 95/31217 A | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | 97/02803 | 1/1997 |
| WO | WO 97/14705 | 4/1997 |
| WO | WO 97/35591 | 10/1997 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | 00/44237 | 8/2000 |

| | | |
|---|---|---|
| WO | 00/44375 | 8/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | 01/13901 | 3/2001 |
| WO | WO 01/19372 | 3/2001 |
| WO | WO 01/22937 | 4/2001 |
| WO | WO 01/35998 | 5/2001 |
| WO | WO 01/46204 | 6/2001 |
| WO | WO 01/58889 | 8/2001 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40034 | 5/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |

OTHER PUBLICATIONS

Gann, P.H. et al., "Lower prostate cancer risk in men with elevated plasma lycopene levels: results of a prospective analysis," Cancer Res. (1999) 59(6):1225-1230.

Min, J. et al., "Effect of apoptosis induced by different vitamin E homologous analogues in human hepatoma cells (HepG2)," J. Hygiene Res. China (2003) 32(4):343-345.

Visarius, T. et al., "Inhibition of human prostate cancer cell proliferation: vitamin E and lycopene targeted pathways regulating cell cycle progression," FASEB J. (2004) 18(8):C103.

Aberg, F. et al., "Distribution and redox state of ubiquinones in rat and human tissues," Arch. Biochem. Biophys. (1992) 295(2):230-234.

Almeida, M.E.M. et al., "Evaluation of soybean oil deodorization distillate for Vitamin E recovery," Arq. Biol. Tecnol. (1994) 37(4):1003-1011.

Barrett, C.W. et al., "The effect of particle size and vehicle on the percutaneous absorption of fluocinolone acetonide," Brit. J. Dermatol. (1965) 77:576-578.

Blom, J.H. et al., "Reproductive success of female rainbow trout (Oncorhynchus mykiss) in response to graded dietary ascorbyl monophosphate levels," Biol. of Reproduction (1995) 52:1073-1080.

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

De Wolfe, F.A. et al., "Ligand-binding proteins: their potential for application in systems for controlled delivery and uptake of ligands," Pharmacol. Rev. (2000) 52(2):207-236.

Devaraj, S. et al., "Modulation of monocyte-macrophage function with alpha-tocopherol: implications for atherosclerosis," Nat. Rev. (2002) 60(1):8-14.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Ernster, L. et al., "Biochemical, physiological and medical aspects of ubiquinone function," Biochim. Biophys. Acta (1995) 1271:195-204.

Octoplus, "Formulation Development of Poorly Soluble Drugs" (www.octoplus.nl) (1999) 2 pages (downloaded Nov. 2008).

Fracalossi, D.M. et al., "Oscars, Astronotus ocellatus, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffen, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Heron-Milhavet, L. et al., "Muscle-specific overexpression of CD36 reverses the insulin resistance and diabetes of MKR mice," Endocrinology (2004) 145:4667-4676.

Kagan, V. et al., "Antioxidant effects of ubiquinones in microsomes and mitochondria are mediated by tocopherol recycling," Biochem. Biophys. Res. Commun (1990) 169(3):851-857.

Karrer, V.P. et al., "d,l-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Langsjoen, P.H. et al., "Overview of the use of CoQ10 in cardiovascular diseases," Biofactors (1999) 9:273-284.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N. Y. Acad. Sci. (2005) 1042:429-438.

Lei, B. et al.,. Progress in alpha-tocopherol preparation technology, Xiandai Huagong (1997) 17(7):13-15.

Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.

Mellors, A. et al., "The inhibition of mitochondrial peroxidation by ubiquinone and ubiquinol," J. Biol. Chem. (1966) 241(19):4353-4356.

Merck Index, The, "α-estradiol" Thirteenth Edition, Whitehouse Station, NJ (2001) p. 660.

Merck Index, The, "Fludarabine to Fludeoxyglucose F18" pages, Thirteenth Edition, Whitehouse Station, NJ (2001) pp. 729-730.

Miyamoto, S. et al., "Synthesis of a novel phosphate ester of a vitamin E derivative and its antioxidative activity," Biosci. Biotech. Biochem. (1998) 62(12):2463-2466.

Morgan, T.M. et al., "Transdermal delivery of estradiol in postmenopausal women with a novel topical aerosol," J. Pharm. Sci. (1998) 87(10):1226-1228.

Morgan, T.M. et al., "Enhanced transdermal delivery of sex hormones in swine with a novel topical aerosol," J. Pharm. Sci. (1998) 87(10):1219-1225.

Mortensen, S.A., "Perspectives on therapy of cardiovascular diseases with coenzyme Q10 (ubiquinone)," Clin. Investig. (1993) 71(Suppl. 8):S116-S123.

Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.

Ostrenga, J. et al., "Significance of vehicle composition I: Relationship between topical vehicle composition, skin penetrability, and clinical efficacy," J. Pharm. Sci. (1971) 60(8):1175-1179.

Owens, D.R. et al., "Alternative routes of insulin delivery," Diabet. Med. (2003) 20:886-898.

Parker et al., "Neonatal vitamin K administration and childhood cancer in the North of England: retrospective case-control study," BMJ (1998) 316:189-193.

Potts, R.O. et al., "Predicting skin permeability," Pharm. Res. (1992) 9(5):663-669.

Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.

Sevast'ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.

Singh, R.B. et al., "Randomized double-blind placebo-controlled trial of coenzyme Q10 in patients with acute myocardial infarction," Cardiov. Drugs Ther. (1998) 12:347-353.

Stedman's Medical Dictionary, "Tocopherol," "Tocotrienol," and "Vitamin K1", 22nd Edition, Williams & Wilkins Co. (1972) p. 1303 and 1400.

Younis et al., "The prevention of type 2 diabetes mellitus: recent advances," Q.J. Med. (2004) 97:451-455.

Iimura, N. et al., "Complex formation between cationic surfactants and insoluble drugs," Bull. Chem. Soc. Jpn. (1999) 72:2417-2422.

Imada, I. et al., "Photochemical reaction of ubiquinone. IV. Coenzymatic activity of ubiquinone and related compounds," Chem. Pharm. Bull. (1965) 13:136-142.

United States Office Action for U.S. Appl. No. 10/416,774 dated Sep. 6, 2007 (9 pages).

United States Office Action for U.S. Appl. No. 10/416,774 dated Jun. 11, 2008 (15 pages).

United States Office Action for U.S. Appl. No. 10/416,774 dated Feb. 17, 2009 (15 pages).

United States Office Action for U.S. Appl. No. 10/416,774 dated Apr. 15, 2009 (14 pages).

United States Office Action for U.S. Appl. No. 10/462,480 dated Dec. 1, 2006 (10 pages).

United States Office Action for U.S. Appl. No. 10/462,480 dated Nov. 1, 2007 (10 pages).

United States Office Action for U.S. Appl. No. 10/462,480 dated Feb. 20, 2009 (17 pages).

United States Office Action for U.S. Appl. No. 10/485,196 dated May 29, 2008 (23 pages).

United States Office Action for U.S. Appl. No. 10/485,196 dated Jul. 23, 2009 (9 pages).

United States Office Action for U.S. Appl. No. 10/486,142 dated Mar. 18, 2008 (12 pages).

United States Office Action for U.S. Appl. No. 10/487,743 dated Dec. 2, 2005 (22 pages).

United States Office Action for U.S. Appl. No. 10/487,743 dated Jul. 27, 2006 (23 pages).

United States Office Action for U.S. Appl. No. 10/498,684 dated Oct. 2, 2008 (21 pages).

United States Office Action for U.S. Appl. No. 10/498,684 dated Jun. 23, 2009 (19 pages).

United States Office Action for U.S. Appl. No. 10/524,090 dated Mar. 12, 2008 (12 pages).

United States Office Action for U.S. Appl. No. 10/542,511 dated Aug. 8, 2007 (19 pages).

United States Office Action for U.S. Appl. No. 10/542,511 dated Mar. 31, 2008 (20 pages).

United States Office Action for U.S. Appl. No. 10/542,511 dated Feb. 5, 2009 (23 pages).

United States Office Action for U.S. Appl. No. 10/551,200 dated Jan. 28, 2009 (11 pages).

United States Office Action for U.S. Appl. No. 10/551,201 dated Jan. 24, 2008 (6 pages).

United States Office Action for U.S. Appl. No. 10/551,203 dated Dec. 6, 2006 (13 pages).

United States Office Action for U.S. Appl. No. 10/551,203 dated Sep. 7, 2007 (13 pages).

United States Office Action for U.S. Appl. No. 10/551,203 dated Apr. 11, 2008 (11 pages).

United States Office Action for U.S. Appl. No. 10/551,203 dated Dec. 19, 2008 (13 pages).

United States Office Action for U.S. Appl. No. 10/551,203 dated Jul. 21, 2009 (21 pages).

United States Patent Office Action for U.S. Appl. No. 09/979,436 dated Apr. 4, 2002 (6 pages).

United States Patent Office Action for U.S. Appl. No. 09/979,436 dated Sep. 23, 2002 (6 pages).

Canadian Patent Office Action for Application No. 2426852 dated Oct., 2008 (2 pages).

Chinese Patent Office Action for Application No. 01818840.0 dated May 28, 2004 (7 pages).

Chinese Patent Office Action for Application No. 01818840.0 dated Jan. 28, 2005 (6 pages).

Chinese Patent Office Action for Application No. 01818840.0 dated Apr. 15, 2005 (6 pages).

Chinese Patent Office Action for Application No. 01818840.0 dated Jul. 22, 2005 (5 pages).

European Patent Office Action for Application No. 01983307.8 dated Jul. 10, 2007 (4 pages).

European Patent Office Action for Application No. 01983307.8 dated Sep. 17, 2008 (2 pages).

Japanese Patent Office Action for Application No. 2002-542406 dated Jul. 29, 2008 (9 pages).

Mexican Patent Office Action for Application No. PA/a/2003/003584 dated Mar. 8, 2006 (6 pages).

Mexican Patent Office Action for Application No. PA/a/2003/003584 dated Oct. 30, 2006 (4 pages).

South Korean Patent Office Action for Application No. 10-2003-7006486 dated Sep. 1, 2005 (4 pages).

South Korean Patent Office Action for Application No. 10-2003-7006486 dated Jan. 17, 2006 (1 page).

* cited by examiner

FORMULATION CONTAINING PHOSPHATE DERIVATIVES OF ELECTRON TRANSFER AGENTS

FIELD OF THE INVENTION

The invention relates to a therapeutic formulation containing phosphate derivatives of electron transfer agents. More particularly, this invention relates to a therapeutic formulation containing mono-(electron transfer agent) phosphate derivatives and di-(electron transfer agent) phosphate derivatives.

The invention also relates to a detergent composition containing surface active agents.

BACKGROUND OF THE INVENTION

In this specification, where a document, act or item of knowledge is referred to or discussed, this reference or discussion is not to be taken as an admission that the document, act or item of knowledge or any combination thereof was at the priority date:

(a) part of common general knowledge; or
 (b) known to be relevant to an attempt to solve any problem with which this specification is concerned.

Whilst the following discussion concerns tocopherol and dermal therapy, it is also to be understood that the same principles apply to any application in which a therapeutic formulation containing electron transfer agents may be used.

The skin is the largest organ of the body, and, among other things, functions to protect the internal organs from external chemical, physical and pathological hazards. Normal skin is composed of an outer epidermis covering sub dermal layers, where each layer comprises different sections. The outer cornified layer of the epidermis possesses properties of strength, flexibility, high electrical impedance and dryness that retards penetration and proliferation of microorganisms. The cornified protective layer is formed by the migration of maturing keratinocytes that are formed at the junction of the dermis and epidermis.

Vitamin E (tocopherol) is an essential part of skin dynamics and is known to be very important for skin health, with deficiency manifesting as a cornified, scaly delicate skin, thickened epidermis, scaling, lesions, chronic infection, inflammation and erythema. Vitamin E is the main naturally occurring lipid soluble agent protecting the skin from stress, and is the main lipid soluble agent protecting the cell membrane lipids from peroxidation.

Skin is subject to constant stress due to exposure to everyday elements—sun, wind and water. As a result, it is common for many topical personal care products such as lotions, moisturizers, shampoo and conditioners to contain vitamin E in various forms to assist in maintaining skin health. In order to assist in maintaining skin health, it is necessary for the vitamin E to reach the target area of the dermis. The most direct method of achieving this targeting is to apply a topical formulation to the affected area. However, topical application of vitamin E to the skin using current formulations has variable success due to the skin's ability to erect an impenetrable barrier to many outside elements. It is critical to provide for the penetration of vitamin E through the epidermis to the dermis.

The use of free tocopherol is avoided because it is unstable, therefore suitable derivatives must be found. In the alimentary canal, it has been found that there is lipase activity which releases free tocopherol from the esters of tocopherol, typically the acetate ester. This lipase activity enables the use of tocopheryl acetate as a nutritional source of Vitamin E.

In contrast, the surface of the skin is deficient in lipase activity unless it is infected with microorganisms that are able to digest sebaceous excretions. Thus tocopheryl acetate must first diffuse through the epidermis into the vital derma, where the cells have a very limited lipase activity which releases the Vitamin E. It is believed that topical formulations using tocopherol acetate have not been able to deliver adequate tocopherol beyond the epidermal layers, and therefore provide little benefit. Since tocopheryl acetate is a lipidic material requiring formulation with an oil in water emulsion, absorption from such a formulation is less than optimal.

The epidermis is permeable to water soluble substances, such as tocopheryl phosphate. Until now producers of formulations containing tocopheryl phosphate utilized mono-tocopheryl phosphate isolated from the mixture produced during phosphorylation. The phosphorylation has been typically achieved using phosphorous oxychloride. The product was purified because it was believed that the by-products were deleterious to the efficacy of the monotocopheryl phosphate because not all the by-products were water soluble. The perceived deleterious effects were considered significant enough to justify the cost of complicated purification processes. Typically, the purification is performed by using ethanol to extract the di-tocopheryl phosphate and free tocopherol by-products.

SUMMARY OF THE INVENTION

It has been found that the use of a non-purified or semi-purified electron transfer agent phosphorylation therapeutic product is efficacious. In particular, the non-water soluble di-(electron transfer agent) phosphate derivatives do not have a deleterious effect on the efficacy of the therapeutic product and may even provide a synergistic effect which results in beneficial properties which enhance the dermal penetration and/or efficacy of the mono-(electron transfer agent) phosphate derivatives.

According to a first aspect of the invention, there is provided a therapeutic emulsion composition comprising the following:

(a) at least one mono-(electron transfer agent) phosphate derivative;
 (b) at least one di-(electron transfer agent) phosphate derivative;
 wherein the amount of mono-(electron transfer agent) phosphate derivative is no less than equimolar to the amount of di-(electron transfer agent) phosphate derivative; and
 (c) a suitable carrier.

According to a second aspect of the invention, there is provided a method for administering to a subject electron transfer agent phosphate derivatives comprising the step of administering a therapeutic emulsion composition comprising the following:

(a) at least one mono-(electron transfer agent) phosphate derivative;
 (b) at least one di-(electron transfer agent) phosphate derivative;
 wherein the amount of mono-(electron transfer agent) phosphate derivative is no less than equimolar to the amount of di-(electron transfer agent) phosphate derivative; and
 (c) a suitable carrier.

The term "electron transfer agent" is used herein to refer to the class of chemicals which may be phosphorylated and which (in the non-phosphorylated form) can accept an electron to generate a relatively stable molecular radical or accept two electrons to allow the compound to participate in a reversible redox system. Examples of classes of electron transfer agent compounds that may be phosphorylated include hydroxy chromans including alpha, beta and gamma tocopherol, tocols and tocotrienols in enantiomeric and raecemic forms; quinols being the reduced forms of vitamin K1 and ubiquinone; hydroxy carotenoids including retinol; and ascorbic acid.

The phosphate derivatives of electron transfer agents comprise compounds covalently bound by means of an oxygen to the phosphorus atom of a phosphate group. The oxygen atom is typically derived from a hydroxyl group on the electron transfer agents. The phosphate derivative may exist in the form of a free phosphate acid, a salt thereof, a di-phosphate ester thereby including two molecules of electron transfer agent, a mixed ester including two different compounds selected from electron transfer agents, a phosphatidyl compound wherein the free phosphate oxygen forms a bond with an alkyl or substituted alkyl group, or a complex with a complexing agent selected from amphoteric surfactant, cationic surfactant, amino acids having nitrogen functional groups or proteins rich in these ammo acids.

Examples of acceptable salts of mono-tocopherol phosphate derivatives are selected from the group consisting of the di-sodium, di-potassium, di-lithium, di magnesium, mono-sodium, mono-potassium, mono-lithium, or mono-magnesium salts or mixtures thereof. Preferably, the acceptable salts of di-tocopheryl phosphate derivatives are selected from the sodium, potassium, lithium or magnesium salts. The di-tocopheryl phosphate derivatives will usually only form a salt in the environment required to form the di-metal salts of mono-tocopheryl phosphate derivatives.

Preferably, the molar ratio of mono-(electron transfer agent) phosphate derivatives to di-(electron transfer agent) phosphate derivatives is in the range from 85:15 to 65:35. There must be enough di-(electron transfer agent) phosphate derivatives to form an emulsion and prevent the mono-(electron transfer agent) phosphate derivatives from going completely into solution, but not so much di-(electron transfer agent) phosphate derivatives that there is precipitation.

The mixture of mono-(electron transfer agent) phosphate derivatives and di-(electron transfer agent) phosphate derivatives can be prepared by recombining the purified individual components or by using the unpurified or semi-purified reaction product of a phosphorylation process. Preferably, the mixture is obtained by using the reaction product of a phosphorylation process. The source of a mixture of tocopheryl phosphate derivatives is preferably the reaction product of the phosphorylation of tocopherol using $P_4O_{10}$.

The term "acceptable carrier" is used herein to refer to a carrier considered by those skilled in the drug, food or cosmetic arts to be non-toxic when used to treat humans, animals or plant in parenteral or enteral formulations. The carrier chosen will depend on the route of administration. Ingestible formulations includes tablets, capsules, powders, chewable tablets, capsules, oral suspensions, children's formulations, enteral feeds, nutraceuticals and functional foods. For a topical application, the carrier typically comprises hydrophilic substances such as water, glycerol, polyethyleneglycol, sorbitol or propanol. For example, the composition could be used as a shampoo, hair conditioner, moisturizing cream or lotion or lipstick as a topical application.

According to a third aspect of the invention, there is a process for preparing a therapeutic emulsion composition containing phosphate derivatives of electron transfer agents comprising the steps of:

(a) phosphorylating one or more electron transfer agents using $P_4O_{10}$ to form a mixture of at least one mono-(electron transfer agent) phosphate derivative and at least one di-(electron transfer agent) phosphate derivative; wherein the amount of mono-(electron transfer agent) phosphate derivative is no less than equimolar to the amount of di-(electron transfer agent) phosphate derivative; and (b) combining the mixture of mono-(electron transfer agent) phosphate derivative and di-(electron transfer agent) phosphate derivative with a suitable carrier.

The mono-(electron transfer agent) phosphate derivatives have good water solubility, therefore before they can be absorbed into the skin or hair an aqueous topically applied composition must dry. In contrast, di-(electron transfer agent) phosphate derivatives are not water soluble and cause the formation of an unstable emulsion when emulsified with water and other hydrophilic solvents. Without wishing to be bound by theory, it is noted that skin is hydrophobic so when the composition is spread onto the skin, the droplets in the emulsion are attracted to the skin. The micelles become unstable near a hydrophobic surface and break so the mono-(electron transfer agent) phosphate derivatives are released onto the skin. The mono-(electron transfer agent) phosphate derivatives can then diffuse through the epidermis into the derma. Therefore, di-(electron transfer agent) phosphate derivatives (once considered a nuisance by-product) function as an effective spreading agent for the mono-(electron transfer agent) phosphate derivatives.

Again, without wishing to be bound by theory, it is considered necessary for a product which is being ingested to have several types of surface activity including detergency and appropriate surface tension to facilitate absorption. mono-(electron transfer agent) phosphate derivatives may have strong detergency but do not have sufficient surface tension effects. Therefore, the mixture of mono-(electron transfer agent) phosphate derivatives and di-(electron transfer agent) phosphate derivatives having self-emulsification properties which include both types of surface activity, that is, strong detergency and strong surface tensions, will be better absorbed, especially in the small intestine.

It has surprisingly further been found that pure mono-tocopheryl phosphate and its salts are powerful surface active agents and detergents giving a stable foam.

According to a fourth aspect of the invention, there is provided a detergent composition comprising a surface active agent selected from the group consisting of mono-tocopheryl phosphate, its salts and mixtures thereof.

There is also provided a method of increasing the surface activity and detergency of a composition by adding a surface active agent selected from the group consisting of mono-tocopheryl phosphate, its salts and mixtures thereof.

Again, whilst not wishing to be bound by theory, it is thought that this detergent property may be due to the fact that mono-tocopheryl phosphate is in the form of a polar head and a non-polar tail. In contrast, di-tocopheryl phosphate has 2 non-polar tails and a polar central group which makes it surface active but it is not a detergent because at high concentrations it accumulates in the surface layer of the composition and acts as a foam breaker because the surface becomes predominantly non-polar.

EXAMPLES

The invention will now be further illustrated and explained by reference to the following non-limiting examples.

Example 1

In this example, a therapeutic formulation according to the invention was prepared using tocopherol as the electron transfer agent.

Preparation of the Tocopheryl Phosphate Mixture

Take 500 g dl-alpha-tocopherol and mix with a high shear mixer 4 aliquots each of 21 g of $P_4O_{10}$ at 12 minute intervals, holding the temperature above 60° C. While the mixture is still hot, add over 1.5 hours 91.5 g of sodium hydroxide which has been dissolved in 62.5 g of water at 50° C. to hydrolyse and neutralise the tocopheryl phosphates. The product was cooled to ambient temperature then further cooled with liquid nitrogen to give a brittle product that was ground to a powder and dried under vacuum.

The mole ratio of mono-tocopheryl phosphate to di-tocopheryl phosphate was approximately 70:30. The product contained mono and di sodium tocopheryl phosphate (approx. 65-85% by mole), sodium di-tocopheryl phosphate (approx. 10-35% by mole) and some sodium di-tocopheryl pyrophosphate.

Preparation and Application of the Topical Formulation

The dried powder was dispersed in water as a 5% solution. 10 ml of this solution was applied to the hands to give a satisfactory application of the tocopheryl phosphates to the skin.

Example 2

The skin penetration properties of a mixture of mono- and di-tocopheryl phosphates according to the invention were compared to tocopheryl acetate.

Test Formulations

The test materials are made up on the basis of 5% mixed actives (mono-tocopheryl phosphate (TP), di-tocopheryl phosphate (T2P) or tocopheryl acetate) in a vehicle consisting of 95/5 distilled water/ethanol with pH adjusted (if necessary to 6.5-7.0 with citric acid or dilute NaOH).

TP and T2P (Mixed Sodium Salts)

A slurry of 6.25 w/w % of 80% mixed TP and T2P in 93.75 w/w % of the 95/5 water/ethanol mixture was prepared.

| Active | TP & T2P (micrograms per applied dose) |
|---|---|
| tocopheryl phosphate | 252 |
| di-tocopheryl phosphate | 1194 |
| tocopherol | 24 |

TP and T2P Complexed

The TPC used was lauryl-imino di-propionic acid tocopheryl phosphate, a surface-active amphotetic phosphate ester complex formed from lauryl imino propionic acid (Deriphat 160) and tocopheryl phosphates. The solution was based on 40% active mixed phosphates as the latter is reacted/combined in a 60/40-amphoteric/mixed-phosphate weight ratio (1.9-1 mole ratio). 12.5 w/w % of the complex was dissolved in 87.5 w/w % of 95/5 water/ethanol mixture.

| Active | TP and T2P complexed (micrograms per applied dose) |
|---|---|
| tocopheryl phosphate | 188 |
| di-tocopheryl phosphate | 713 |
| Tocopherol | 20 |

Tocopheryl Acetate

Tocopheryl acetate is obtained from Roche/BASF. 5.0 w/w % of tocopheryl acetate was dispersed in 95.0 w/w % of 95/5 water/ethanol mixture.

Method

The test formulations are evaluated in in vitro human skin penetration studies. Samples are analyzed for the mono- and di-tocopheryl phosphates, free alpha-tocopherol, and tocopheryl acetate by high performance liquid chromatography (HPLC). The tests ate conducted by DermTech International (San Diego, Calif.). Human cadaver skin samples are obtained and prepared. Each formulation is evaluated on triplicate sections from each donor at a topically applied dose of 5 µL/cm². Receptor solutions are collected over 48 hours at pre-selected time intervals. After 48 hours the skin surface is washed with isopropyl alcohol, and the skin is collected and split into epidermis and dermis. The skin sections are extracted with isopropyl alcohol. All collected samples are processed and assayed for tocopherol, tocopheryl acetate, tocopheryl phosphate and di-tocopheryl phosphate.

Mass balance from the samples is between 80-120% of the applied dose.

No tocopherols are observed in the receptor solution. This could be a result of amounts being below limits of detection, or degradation of the various tocopherol species into other, as yet uncharacterized, compounds.

TABLE 1

SKIN PENETRATION STUDY
(Percent Distribution of Tocopherols Recovered; wt/wt %).

| Treatment | α-Tocopherol | TP | T₂P |
|---|---|---|---|
| TP & T2P (mixed sodium salts) | | | |
| Surface wash | 65.05 | 41.40 | 56.05 |
| Epidermis | 26.74 | 47.06 | 37.31 |
| Dermis | 8.24 | 11.42 | 6.62 |
| Dermis/Epidermis Ratio | 0.31 | 0.24 | 0.18 |
| TP & T2P complexed | | | |
| Surface wash | 50.00 | 48.82 | 70.92 |
| Epidermis | 35.99 | 24.55 | 16.67 |
| Dermis | 14.07 | 26.62 | 12.36 |
| Dermis/Epidermis Ratio | 0.39 | 1.08 | 0.74 |
| Tocopherol Acetate | | | |
| Surface wash | 91.48 | | |
| Epidermis | 7.13 | | |
| Dermis | 1.39 | | |
| Dermis/Epidermis Ratio | 0.20 | | |

Conclusions

The results demonstrate that the inclusion of 20 to 30% of T2P in the formulation did not have a deleterious effect on the performance of the tocopheryl phosphate product. Further, both of the TP/T2P mixtures were more efficiently transported into the dermis than the tocopheryl acetate product

Example 3

In this example, a mixture was prepared comprising mono-ubiquinyl phosphate and di-ubiquinyl phosphate made according to the invention.

100 g of ubiquinone was partially dissolved in 200 ml of hot glacial acetic acid. To the vigorously stirred solution, small amounts of zinc (total of 30 g) were added until the solution changed from yellow to green and then became colorless. The hot solution was filtered and the unreacted zinc was washed 2 more times (50 ml) with hot glacial acetic acid to recover any remaining ubiquinol. Glacial acetic acid was removed from the ubiquinol by vacuum distillation or by cooling the solution to 0° C. and filtering off the crystallized ubiquinol. To further remove any traces of acetic acid, the ubiquinol was placed under high vacuum (1 mm Hg) for a period of 2 hours.

The ubiquinol product was treated immediately by heating to 100° C. and adding 33 g of $P_4O_{10}$. The mixture was stirred for 3 hours and then 500 mm water was introduced slowly into the mixture. The temperature of the reaction was maintained just below boiling point for a further 1 hour. Removal of water yielded ubiquinyl phosphates and phosphoric acid. The phosphoric acid was partially removed by further washes with hot water.

The final product consisted of 139 g of mono-ubiquinyl phosphate, di-ubiquinyl phosphate and phosphoric acid. The product was analyzed by $^{31}P$ NMR and the molar ratio of mono-ubiquinyl phosphate: di-ubiquinyl phosphate was 76:24.

Example 4

In this example, the surface active properties of mono-tocopheryl phosphate was investigated.

0.1 g of pure di-sodium mono-tocopheryl phosphate was dissolved in 10 ml of pure distilled water in a 50 ml cylindrical stoppered vessel. The vessel was shaken on a test tube agitator and the headspace filled with stable foam. The foam was examined on a daily basis and showed complete stability for one day and then slowly degraded over the rest of the four-day period.

Mono-tocopheryl phosphate is therefore a surface active agent with detergent properties.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

What is claimed is:

1. An emulsion composition for therapeutic administration comprising:
   (a) at least one mono-(electron transfer agent) phosphate compound;
   (b) at least one di-(electron transfer agent) phosphate compound; and
   (c) a suitable carrier;
   wherein the molar ratio of the at least one mono-(electron transfer agent) phosphate compound to the at least one di-(electron transfer agent) phosphate compound is in the range of 85:15 to 65:35; and
   wherein the electron transfer agent is selected from the group consisting of hydroxy chromans including alpha, beta, and gamma tocopherols, tocols and tocotrienols; quinols being the reduced forms of vitamin K1 and ubiquinone; hydroxy carotenoids including retinol; and ascorbic acid.

2. The composition according to claim 1 wherein the electron transfer agent is alpha-tocopherol, a salt thereof, or a mixture thereof.

3. The composition according to claim 1 wherein the at least one mono-(electron transfer agent) phosphate compound and the at least one di-(electron transfer agent) phosphate compound are complexed with a complexing agent selected from amphoteric surfactants, cationic surfactants, amino acids having nitrogen functional groups and proteins rich in these amino acids.

4. A method for administering to a subject electron transfer agents, the method comprising the step of administering a therapeutic emulsion composition comprising:
   (a) at least one mono-(electron transfer agent) phosphate compound;
   (b) at least one di-(electron transfer agent) phosphate compound; and
   (c) a suitable carrier;
   wherein the molar ratio of mono-(electron transfer agent) phosphate compound to di-(electron transfer agent) phosphate compound is in the range of 85:15 to 65:35; and
   wherein the electron transfer agent is selected from the group consisting of hydroxy chromans including alpha, beta, and gamma tocopherol, tocols and tocotrienols; quinols being the reduced forms of vitamin K1 and ubiquinone; hydroxy carotenoids including retinol; and ascorbic acid.

5. A process for preparing a therapeutic emulsion composition containing electron transfer agent phosphate compounds comprising the steps of:
   (a) phosphorylating one or more electron transfer agents using $P_4O_{10}$ to form a mixture of at least one mono-(electron transfer agent) phosphate compound and at least one di-(electron transfer agent) phosphate compound;
   wherein the molar ratio of mono-(electron transfer agent) phosphate compound to di-(electron transfer agent) phosphate compound is in the range of 85:15 to 65:35; and
   (b) combining the mixture of mono-(electron transfer agent) phosphate compound and di-(electron transfer agent) phosphate compound with a suitable carrier,
   wherein the electron transfer agent is selected from the group consisting of hydroxy chromans including alpha, beta, and gamma tocopherol, tocols and tocotrienol; quinols being the reduced forms of vitamin K1 and ubiquinone; hydroxy carotenoids including retinol; and ascorbic acid.

6. A topical emulsion composition for topical application comprising:
   (a) at least one mono-(tocopheryl) phosphate compound;
   (b) at least one di-(tocopheryl) phosphate compound; and
   (c) a suitable carrier,
   wherein the molar ratio of mono-(tocopheryl) phosphate compound to di-(tocopheryl) phosphate compound is in the range of 85:15 to 65:35.

7. The composition according to claim 1 wherein the mono-(electron transfer agent) phosphate compound is a surface active agent selected from the group consisting of mono-(tocopheryl) phosphate, or a salt thereof, or a mixture thereof.

8. The composition according to claim 1 wherein the mono-(electron transfer agent) phosphate compound increases the surface activity and detergency of the therapeutic emulsion composition.

9. The composition according to claim 1 wherein the electron transfer agent is tocopherol.

10. The composition according to claim 1 wherein the electron transfer agent is selected from the group consisting of α-tocopherol, β-tocopherol, δ-tocopherol, tocols, and tocotrienols.

11. The composition according to claim 3 wherein the complexing agent is lauryl-imino di-propionic acid or arginine.

12. The composition according to claim 1 wherein the molar ratio of the at least one mono-(electron transfer agent) phosphate compound to the at least one di-(electron transfer agent) phosphate compound is 70:30.

13. The composition according to claim 1 wherein the at least one di-(electron transfer agent) phosphate compound is a mono-phosphate.

14. The composition according to claim 6 wherein the at least one di-(tocopheryl) phosphate compound is a mono-phosphate.

* * * * *

UNITED STATES PATENT AND TRADEMARK OFFICE
CERTIFICATE OF CORRECTION

PATENT NO.       : 7,648,710 B2                                    Page 1 of 1
APPLICATION NO.  : 10/416775
DATED            : January 19, 2010
INVENTOR(S)      : Simon Michael West It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 518 days.

Signed and Sealed this

Twenty-third Day of November, 2010

David J. Kappos
*Director of the United States Patent and Trademark Office*